United States Patent [19]

Khwaja

[11] Patent Number: 5,780,037
[45] Date of Patent: Jul. 14, 1998

[54] MISTLETOE EXTRACT AND METHOD

[75] Inventor: Tasneem A. Khwaja, Newport Beach, Calif.

[73] Assignees: PharmaPrint, Inc.; The University of Southern California, both of San Diego, Calif.

[21] Appl. No.: 796,487

[22] Filed: Feb. 5, 1997

Related U.S. Application Data

[60] Continuation of Ser. No. 579,832, Dec. 28, 1995, abandoned, which is a division of Ser. No. 421,993, Apr. 14, 1995, abandoned.

[51] Int. Cl.$^6$ .................................................. A61K 35/78
[52] U.S. Cl. .................................................. 424/195.1
[58] Field of Search .................................................. 424/195.1

[56] References Cited

U.S. PATENT DOCUMENTS

| | | | |
|---|---|---|---|
| 3,394,120 | 7/1968 | Vester | 530/379 |
| 3,472,831 | 10/1969 | Vester | 530/379 |
| 3,475,102 | 10/1969 | Vester | 530/379 |
| 5,401,502 | 3/1995 | Wunderlich et al. | 424/195.1 |

FOREIGN PATENT DOCUMENTS

| | | |
|---|---|---|
| 602 686 | 6/1994 | European Pat. Off. |
| 235 418 | 5/1986 | Germany. |
| 42 21 836 | 1/1994 | Germany. |
| 42 29 876 | 3/1994 | Germany. |

OTHER PUBLICATIONS

Gawlik et al., 1992, "Antiproliferative Effect of Mistletoe-Extracts In Melanoma Cell Lines", Anticancer Research 12(6A):1882.
E. Jordan and H. Wagner, "Structure and Properties of Polysaccharides from Viscum album", Oncology 43:(1)8–15, 1986.
Wren, Potter's Cyclopedia, p. 236, 1952.

*Primary Examiner*—Jean C. Witz
*Attorney, Agent, or Firm*—Pennie & Edmonds LLP

[57] ABSTRACT

A method for making and identifying mistletoe extracts as being of a pharmaceutical grade which is useful in treating AIDS, cancers and other diseases where the immune system is suppressed. The method is based on the discovery of five marker proteins which selectively bind with different sugars. Pharmaceutical grade extracts in accordance with the invention require certain concentration levels of each protein. An additional further requirement is that each protein fraction must meet specific bioactivity levels with respect to preventing malignant cell proliferation. Fingerprint markers with respect to viscotoxins and alkaloids present in the extract are also provided. Methods of treatment using the pharmaceutical grade mistletoe are disclosed.

16 Claims, 1 Drawing Sheet

FIG. 1

MISTLETOE EXTRACT AND METHOD

BACKGROUND OF THE INVENTION

This application is a continuation application of U.S. patent application Ser. No. 08/579,832, filed Dec. 28, 1995, now abandoned, which is a divisional of U.S. Ser. No. 08/421,993, filed Apr. 14, 1995, now abandoned.

FIELD OF THE INVENTION

The present invention relates generally to the preparation of mistletoe extracts and methods for making such extracts in a medicinally useful and pharmaceutically acceptable form. More particularly, the present invention relates to methods for making and using mistletoe extracts wherein certain marker proteins are utilized to control the quality and clinical use of the extracts. These marker proteins provide a measure of the extracts effectiveness in treating certain diseases. The extract is either accepted or rejected as a pharmaceutical grade composition depending upon the amounts and/or biological activity of the various protein markers which are present in the extract and the intended clinical use.

DESCRIPTION OF RELATED ART

Mistletoe belongs to the genus Viscum (family, Loranthaceae) which includes a variety of semiparasitic plants found all over the world. Mistletoe is a parasite which grows on a variety of deciduous trees including apple, cherry, oak, ash hawthorn, lime and acorn. Mistletoe and extracts of mistletoe have been used for centuries in a wide variety of therapeutic settings. The effectiveness of mistletoe as a remedy for treating a multitude of ailments has been the subject of a great deal of folklore, superstitions and mystical accounts. Although many of the early uses for mistletoe may have been based more on fantasy than on fact, the reputation of mistletoe as a powerful elixir is well deserved because this parasitic plant contains a rather large variety of complex and pharmacologically potent ingredients.

Beginning in the early 1900's, mistletoe and the pharmacological properties of extracts from mistletoe have been subjected to a more rigorous scientific investigation. In particular, mistletoe extracts have been suggested for use in treating a variety of specific diseases including cardiovascular illnesses, especially hypertension and arteriosclerosis; cancer and arthrosis. Fermented mistletoe extracts marketed under the tradenames ISCADOR®, HELIXOR® and PLENOSOL® have been proposed for use in treating a number of specific diseases. ISCADOR® and HELIXOR® have been injected subcutaneously while PLENOSOL® has been administered both intracutaneously and intravenously. These three commercially available preparations are derived from mistletoe found in Europe, *Viscum album L.*

Since 1980, the investigation of mistletoe has increased due to its immunomodulatory properties and potential usefulness in treating cancer. See International Journal of Cancer Research Treatment-ONCOLOGY-Vol. 43, Supplement 1, 1986. A major problem facing mistletoe investigators involves the analysis, identification and standardization of the pharmacologically active ingredients in mistletoe and extracts thereof. This problem is exacerbated by the fact that the numerous complex ingredients which are found in mistletoe extracts vary widely in type and amount depending upon the species of mistletoe, the location where the plant is grown, the time of year when the plant is harvested, the particular host tree, the extraction procedure used and a number of other factors.

The principal classes of ingredients in mistletoe which have been found to provide pharmacological activity include lectins, phenylpropans, viscotoxins, alkaloids, flavonoids, lignans, amines, phenyl carboxylic acids and polysaccharides. Although the types of pharmacologically important compounds which are generally present in mistletoe have been identified, investigators have not had a great deal of success with respect to standardizing the multitude of available extracts to establish if one or more ingredients are responsible for the observed bioactivity and whether the ingredients act together or may be effective individually. The extremely diverse nature of mistletoe extracts and the inherent variability in extract compositions makes it difficult to use the extracts to conduct clinical investigations. Standardization of the pharmaceutical agent is essential in order to produce meaningful clinical data. Further, identification and standardization of the active ingredients in mistletoe extracts are also important in the routine treatment of patients. It is imperative that the mistletoe extract be of consistent and verifiable quality to insure that dosage levels and treatment protocols are effective.

As is apparent from the above, mistletoe and extracts prepared therefrom are potent pharmacological agents which require further investigation. As part of this continuing investigation of the medicinal and pharmacological properties of the numerous mistletoe varieties from around the world, there is a need to provide standardization of the quality of mistletoe extracts. Further, it is essential that the extracts which are used in various clinical studies and treatment protocols also be standardized and that quality control programs be instituted.

SUMMARY OF THE INVENTION

In accordance with the present invention, a method is provided for making pharmaceutical grade mistletoe extract. The term "pharmaceutical grade" when used in this specification means that certain specified pharmacologically active ingredients in the mistletoe extract must be within certain specified absolute and/or relative concentration limits and/or that the ingredients must exhibit certain activity levels as measured by a given bioactivity assay.. The pharmaceutical grade mistletoe extracts made by the method of the present invention are particularly well-suited for use in clinical studies and treatment of patients in general. The method insures that the extract being used as the basis for a particular treatment protocol will be effective for its intended purpose.

The method of the present invention is based upon the discovery that certain marker proteins provide the majority of the bioactivity demonstrated by mistletoe extracts with respect to certain cancer and AIDS treatments. The marker proteins have also been referred to as lectins. The marker proteins are sugar-binding proteins which bind selectively with lactose, galactose, melibiose, N-acetyl-D-galactosamine or fucose. The method insures that mistletoe extracts are prepared and used for treatment of AIDS cases and certain cancers only if they contain specified levels of these sugar-binding proteins and/or only if the proteins exhibit a minimum level of bioactivity as measured by their ability to inhibit the growth of selected cancer cells.

The method involves the step of first preparing a powder of mistletoe. The mistletoe powder is then extracted with an aqueous solution to form an aqueous extract. The powdered mistletoe or mistletoe residue may also be obtained by lyophilizing a known volume of mistletoe extract/solution which is to be standardized. The concentration may be expressed as mg plant material/ml or assayed for protein contents and described as µg or mg protein per ml of the solution. A portion of the aqueous extract is analyzed to determine the concentration in mg/ml of one or more proteins which bind to lactose, galactose, melibiose, N-acetyl-D-galactosamine or fucose. The proteins are also further segregated based on whether they are dependent on calcium ion for binding. The sugar-binding proteins may also be analyzed to determine the concentration of protein which is required to inhibit growth of a selected cancerous cell line, such as the leukemia cell line-L1210. The final step in the method involves identifying the extract as being of pharmaceutical grade, i.e. either accepting or rejecting the extract for use in specified treatment protocols. The final step involves determining whether the extract has sugar-binding protein levels within certain concentration and/or activity limits. In effect, the extract must meet a required sugar-binding protein fingerprint in order to be identified as pharmaceutical grade for a particular treatment protocol.

The extract as a whole may be initially assayed for its activity in the murine leukemia L1210 cell culture system. This activity, described in "activity units", may be used as an initial screening step to determine if the extract is potent enough to be considered for further testing to establish whether or not it is of pharmacological grade in accordance with the present invention.

As a feature of the present invention, the method is well-suited for insuring consistent quality and bioactivity of mistletoe extracts used in the treatment of AIDS and other disorders of the immune system. The extracts may also be used to treat specific cancers, such as breast, lung, colon and a variety of other malignancies. In general, the levels of all five of the $Ca^{++}$ dependent sugar-binding proteins will be between about 0.01 to 1.0 mg/ml with inhibitory activities of between about 0.001 to 0.5. The general levels of non-$Ca^{++}$ dependent sugar-binding proteins will be about 0.10 to 2.0 mg/ml with inhibitory activities of between about 0.0001 to 0.5 µg/ml. It was found that extracts having these particular ranges of sugar-binding proteins are effective in treating AIDS patients, cancer, post-operative malignancies and post chemotherapy patients.

As a further feature of the present invention, it was discovered that unfermented mistletoe extracts contained protein concentrations and inhibitory concentration levels which met the pharmaceutical grade requirements set forth above whereas fermented mistletoe extracts did not. Additionally, it was discovered that mistletoe belonging to the species *Viscum album coloratum* which is found in South Korea growing on oak trees may be extracted with an aqueous solution to produce extracts which are consistently within the limits stated above for pharmaceutical grade products. This invention is also useful in standardization of "fermented" extracts of *Viscum album L.* like ISCADOR.

Another feature of the invention is that biologically active residual non-sugar binding proteins (viscotoxins) and alkaloids (nitrogenous compounds which give positive test with Dragendorff reagent) can be separated and quantified on the basis of protein content or weight, respectively, to provide further fingerprint markers. In a preferred embodiment of the invention, extracts must not only meet the lectin fingerprint requirements in order to be identified as pharmaceutical grade, but they must also have an alkaloid fraction content of about 10 to 50 µg per 1 ml of extract where the extract is a 1 percent extract, i.e. 1 gram of plant material extracted with 100 ml of aqueous solution. They must also have a viscotoxin content of about 10 to 40 µg per ml of 1% extract.

The present invention provides the ability to closely control the quality and clinical effectiveness of mistletoe extracts. Specific sugar-binding protein fingerprints are presented as one aspect of the invention. These protein fingerprints are useful for determining if a particular mistletoe extract meets levels of pharmacological activity and composition requirements for a particular treatment regimen. Such a determination is important to insure that clinical studies and patient treatment with mistletoe extracts are based on consistent and verifiable extract composition parameters.

The above discussed and many other features and attendant advantages of the present invention will become better understood by reference to the following detailed description when taken in conjunction with the accompanying drawings.

DETAILED DESCRIPTION OF THE INVENTION

The present invention is a method for producing pharmaceutical grade extracts of mistletoe which are effective in the treatment of AIDS and certain cancers. The method requires that the mistletoe extract be an aqueous extract which meets certain requirements with respect to protein concentration, content and pharmacological activity.

"Pharmaceutical grade", for the purposes of this specification, means that certain specified pharmacologically active ingredients in the mistletoe extract must be within certain specified absolute and/or relative concentration limits and/or that the ingredients must exhibit certain activity levels as measured by a given bioactivity assay. In one embodiment, the aqueous mistletoe extract contains between about 0.01 and 1.0 mg/ml of at least one $Ca^{++}$ dependent sugar-binding protein which is capable of binding with lactose, galactose, melibiose, N-acetyl-D-galactosamine or fucose. Preferably, the one or more $Ca^{++}$ dependent sugar-binding proteins must exhibit an inhibitory concentration of below about 0.50 µg/ml. "Inhibitory concentration", as used in this specification is a measure of the sugar-binding protein's ability to inhibit the in vitro growth of certain cancerous cell lines. The inhibitory concentration is expressed in µg of sugar-binding protein per ml of extract solution which is required to cause a 50% inhibition of the growth of a particular cancerous cell line. The preferred cell line which is used to measure inhibitory concentrations is a leukemia cell line identified as L1210. This particular cancerous cell line is available from a number of commercial sources. L1210 cells have been used in the past as a screening system for testing drug efficacy. Details regarding the culturing and growth of L1210 cell is described in a number of scientific articles including ONCOLOGY, Vol. 43/S1/86 at pages 42–50 and Experientia 36 (1980) pages 599–600. Other cell lines which can be used to determine inhibitory concentrations include KB cells or other rapidly growing cell lines which demonstrate repeatable results. Other parameters like inhibition of macromolecule synthesis in a given cell culture line may be used.

To be identified as Pharmaceutical Grade, the extract must also contain one or more $Ca^{++}$ non-dependent sugar-binding proteins which are capable of binding with lactose, galactose, melibiose, N-acetyl-D-galactosamine or fucose. The level of the $Ca^{++}$ non-dependent sugar-binding proteins must be between about 0.1 and 2.0 mg/ml. The inhibitory activity of the one or more $Ca^{++}$ non-dependent sugar-binding proteins is preferably below about 0.5 µg/ml.

In accordance with the present invention, mistletoe powder is prepared according to any of the known powdering procedures. Any type of mistletoe may be used, however, to maintain the rejection rate of extracts at a low level, it is preferred that the mistletoe extract be prepared from the *Viscum album, coloratum* species which is found on oak trees in and around Seoul, South Korea or the *Viscum album L.* species which is commonly found throughout Europe. Further, it is preferred that the mistletoe be flash frozen shortly after harvesting and then ground to a powder in the frozen state. Flash freezing with liquid nitrogen or similar cryogenic liquid is preferred. The entire mistletoe plant may be used in preparing the powder. The preferred harvesting time is when the berries are ripe. Due to the variable and relatively unknown nature of all of the complex ingredients in mistletoe, it is preferred that all of the above listed preferred steps be followed in order to optimize the number of extract preparations which meet the requirements of the method of the present invention. The fresh soft part of the mistletoe plant (including leaf, stem and/or berries) may be pressed to squeeze the cell-sap, which on dilution with water or sterile physiological saline will provide an aqueous extract.

The mistletoe powder is extracted using a substantially pure aqueous solution. The extracting solution may include additional ingredients to enhance the extraction process. The extract may include a salt such as calcium chloride or sodium chloride in an amount sufficient to enhance extraction of proteins from the mistletoe sap. Salt concentrations on the order of 0.02M are preferred. Detergents such as TRITON® x-100 may also be added to enhance extraction of protein from the plant cell walls. The extractant is preferably buffered with 0.02M Tris to a pH of about 7.8. The extraction procedure should utilize an amount of extractant relative to the amount of mistletoe being extracted which will produce levels of proteins as set forth below. Preferably, between about 100 and 400 grams of mistletoe powder will be extracted with between about 1000 and 4000 ml of aqueous solution. The powder is mixed in the solution and left to stand for from one to four hours. The powder particulates remaining after the extraction period are separated by filtration, centrifugation or other conventional separation technique to produce the aqueous mistletoe extract.

The mistletoe extract, prior to pharmacological analysis of its contents, is preferably assayed for its overall biological activity. The biological evaluation of the extract is carried out on the basis of its inhibition of the growth of mouse leukemia L1210 in culture. From this initial test, the $ID_{50}$ (concentration in µg/ml of the extract which will cause 50% inhibition in the growth of L1210 cells as compared to untreated controls) of the extract is determined. The biological activity of the extract is expressed in terms of "activity units" (A.U.), which represent ratio of concentration of the extract (expressed in µg extract/ml) to its $ID_{50}$ value (µg/ml). To pass this initial step of extract evaluation, 1 ml of 1% extract (10 mg total extract) must contain 100 or more activity units. Extracts with lower than 100 A.U. values are rejected, and those with a passing grade are further analyzed to established specific values and ratios of its biologically active components as described below.

Figure 1:
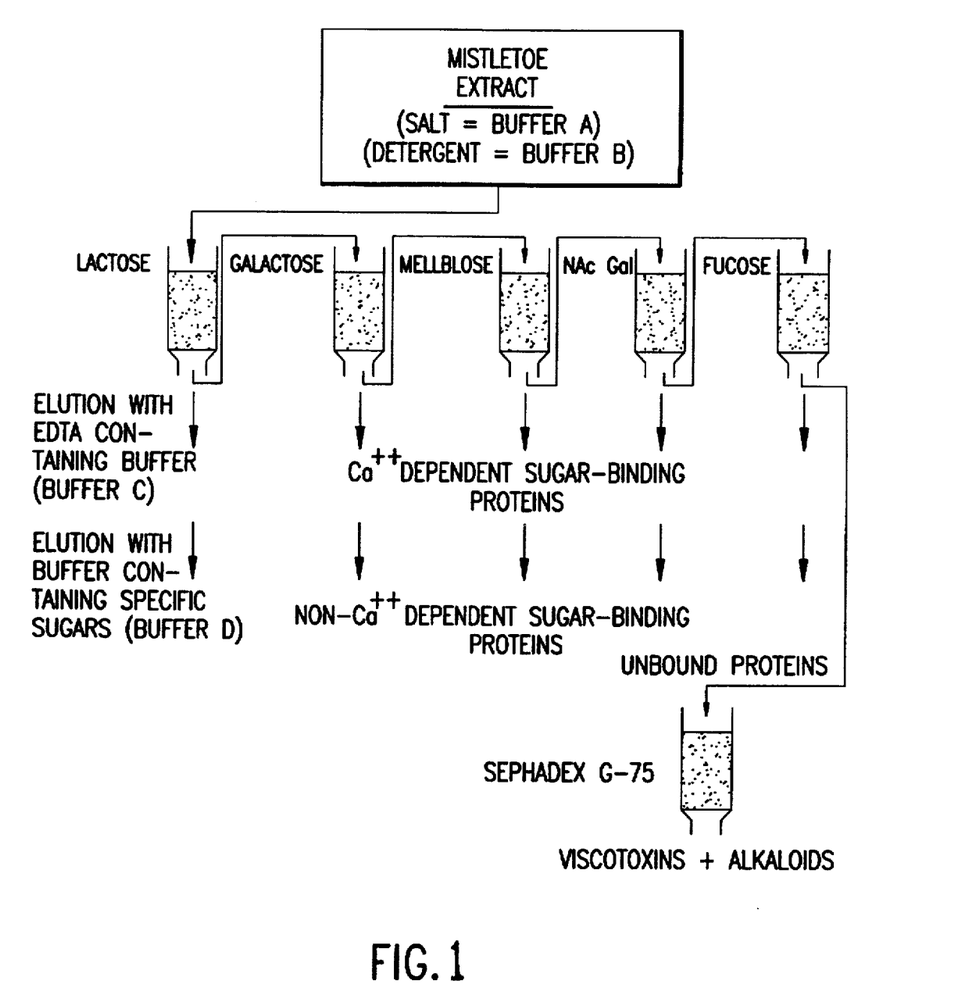
The FIGURE is a schematic representation of a preferred exemplary extraction procedure which produces an aqueous extract which is analyzed in accordance with the quality assurance method of the present invention.

In accordance with the present invention, a portion of the mistletoe extract is further analyzed to determine the concentration of one or more sugar-binding proteins in the extract. The analysis is preferably conducted by affinity column chromatography as schematically represented in the FIGURE. The analysis is preferably conducted in two stages in order to separate the proteins which require $Ca^{++}$ for binding to sugar and those proteins which are non-$Ca^{++}$ dependent. A Buffer which contains ethylene diamine tetraacetic acid (EDTA) or other chelating agent is used to elute the $Ca^{++}$ dependent sugar-binding proteins from affinity columns which have been treated with the specific sugars of interest, i.e. lactose, galactose, melibiose, N-acetyl-N-galactosamine and fucose. The resulting fractions are then analyzed for protein content. Other affinity columns based on similar principles of chromatography may also be used, e.g. mannose, rhamnose, maltose, asialofeutin, glucosamine and n-acetyl glucosamine. The appropriate levels and activities of the lectins in the extract which are specific for these sugars can be established by measuring their levels in extracts which meet the criteria for sugar-specific lectins set forth above.

After elution of each of the sugar-specific affinity columns with EDTA-containing buffer, the columns are then eluted with buffers that each contain the sugar which corresponds to the sugar bound to the respective affinity columns. Sepharose® 4B is a preferred column material. The various fractions resulting from this second elution contain the non-Ca++ dependent sugar-binding proteins. The protein content of each of these fractions is also quantitatively determined. Protein quantitation can be performed using any of the conventional quantitative analytical procedures including ninhydrin based tests, spectroscopic determination and Bio-Rad or Pierce analysis. The use of multiple buffers as described above is preferred so that the total level of each type of protein is determined. Affinity column chromatography is preferred because it is a conventional separation technique which is well-known to those of ordinary skill in the art and which is well-suited for separating the proteins from the extract based on their sugar-binding specificity. Other separation procedures may be utilized provided that an accurate measurement of each of the selected sugar-binding proteins is provided.

An alternate method for analyzing the lectin (sugar-binding protein) content, alkaloidal fraction and viscotoxin levels in the extract involves the use of ammonium sulfate. In this method, the total proteins of mistletoe preparation is precipitated with 70% ammonium sulfate. The preparation is centrifuged and the precipitate which contains a mixture of the viscotoxins and the sugar-binding proteins (lectins). This mixture is separated on a acid-hydrolysed Sepharose 4B column. The bound lectins can be eluted from the column with buffers containing specific sugars as described above. Affinity chromatography to identify the specific sugar-binding proteins can be carried out as also described above. The unbound proteins which initially fan through the column contain viscotoxins which are quantitated according to conventional protein quantitative analysis.

The ammonium sulfate-supernatant, which contains the alkaloidal fraction, is lyophilized and the alkaloids are extracted with chloroform. The chloroform residue provides the total alkaloids which are also quantitated by weighing or conventional method.

The five $Ca^{++}$ dependent and non-$Ca^{++}$ dependent sugar-binding proteins which are measured in accordance with the present invention are those that bind with lactose, galactose, melibiose, N-acetyl-D-galactosamine or fucose. The concentration of each of the sugar binding proteins (both Ca++ dependent and non-Ca++dependent) is between 0.1 and 2.8 weight percent of the total protein content of the extract. The specific relative weight percent ranges which are necessary for an extract to meet the requirements of the present invention are set forth in Table 6. Tables 7 and 8 set forth the weight percent ranges for pharmaceutical grade extracts prepared from European and Korean mistletoe, respectively.

The relative percentage of each sugar-binding protein with respect to the total protein content of the extract will remain fairly constant irrespective of extraction conditions. However, the actual concentration levels of the various sugar-binding proteins will vary in each extract depending upon a number of factors including the relative amounts of mistletoe and aqueous extractant, the length of extraction and temperature. It is preferred that the extract be analyzed to determine the concentration levels of the various specified sugar-binding proteins and that these concentration levels be used as the primary method of determining whether an extract meets the pharmaceutical grade requirements of the present invention. However, the extract may be diluted or concentrated to achieve protein concentration levels outside the preferred concentration ranges provided that the relative percentages of the sugar-binding proteins remain within the limits set forth in Table 6, for general mistletoe extracts, and Tables 7 and 8 for European and Korean mistletoe extracts, respectively. The extract, once it has been identified as pharmaceutical grade, may be dehydrated, and stored as a powder for rehydration and use at a later time to treat AIDS or cancer.

The preferred concentration level of the $Ca^{++}$ dependent sugar-binding proteins in the extract is within the range of about 0.01 to 1.0 mg/ml. The method of the present invention can be carried out by measuring only one of the $Ca^{++}$ dependent sugar-binding proteins to establish if the extract is within pharmaceutical grade limits. However, it is preferred that two or more of the sugar-binding protein levels be measured, e.g. galactose, lactose and/or N-acetyl-D-galactosamine specific proteins. Even more preferably, the extract is analyzed to determine if the concentration levels of all five $Ca^{++}$ dependent sugar-binding proteins meet the above concentration limits. The method can also be carried out by measuring various, combinations of 3 or 4 of the specified $Ca^{++}$ dependent sugar-binding proteins. Concentration ranges and inhibitory activity ranges are set forth in Tables 9, 10 and 11.

The concentration level of the non-$Ca^{++}$ dependent sugar-binding proteins in the extract must be within the range of about 0.10 to 2.0 mg/ml. The method of the present invention can be carried out by measuring only one of the non-$Ca^{++}$ dependent sugar-binding proteins to establish if the extract is within pharmaceutical grade limits. However, as above, it is preferred that two or more of the non-$Ca^{++}$ dependent sugar-binding protein levels be measured. Even more preferably, the extract is analyzed to determine if the concentration levels of all five non-$Ca^{++}$ dependent sugar-binding proteins meet the required concentration limits. The most preferred method involves determining the complete protein finger print, i.e. the protein concentration in all ten sugar-binding protein fractions. In this most preferred embodiment, the extract is not identified or otherwise considered to be a pharmaceutical grade extract unless all ten protein fractions have the required concentration levels set forth above. The fingerprint parameters are set forth in Tables 9, 10 and 11.

The bioactivity of the various protein fractions may be used alone or in combination with their respective concentration levels to identify the extract as pharmaceutical grade in accordance with the present invention. The various proteins which make up each of the $Ca^{++}$ dependent sugar-binding protein groups must each exhibit an inhibitory concentration of between about 0.001 and 0.5 μg/ml. The proteins which make up each of the non-$Ca^{++}$ dependent sugar-binding groups must also each exhibit an inhibitory concentration of between about 0.0001 and 0.5 μg/ml.

The method for measuring inhibitory action is set forth in numerous scientific articles including the references mention previously. It is preferred that the inhibitory action be measured in vitro with respect to leukemia L1210 cells. This procedure is preferred because L1210 cells are readily available, they are easily maintained by well-known culturing procedures and provide consistently reproducible results. The inhibitory concentration of each sugar-binding protein fraction is determined by adding increasing amounts of the fraction and determining when cell growth is inhibited by 50% as compared to a control culture. It is preferred that both the concentration level and the inhibition concentration of each of the sugar-binding proteins be measured and that they all be within the ranges set forth above and in Tables 9, 10 and 11 in order for the extract to be identified as pharmaceutical grade in accordance with the present invention.

Once the concentration levels and/or inhibitory concentration of the designated sugar-binding proteins has been established, the extract is either identified as pharmaceutical grade if the above limits are met. If one or more requirements are not met, the extract is rejected. The extracts which are identified as pharmaceutical grade are then used in treatment programs for treating diseases such as AIDS and cancer. The pharmaceutical grade extracts are not only useful in treating AIDS, but they may be used to treat any individual with a suppressed immune system. If the extract has protein levels which are above the limits set forth above, the extract may be diluted as required to bring the extract protein concentrations down to the established limits. If the extract protein levels are below the limits, the extract is rejected and not identified as pharmaceutical grade.

It is preferred that the extract be initially screened for overall activity before beginning the more rigorous analysis of the sugar-binding protein fingerprint. It was discovered that extracts which do not meet certain total activity levels will also not meet the more specific protein fingerprint requirements of the present invention. The activity units are determined in the same manner as for the individual protein fraction with the only difference being that the entire extract is being tested. In accordance with the present invention, the extract must have and activity of greater than 100 AU. Table 12 sets forth the results of initial screening wherein a number of different mistletoe extracts were screened to determine their biological activity using the L1210 cells as previously described. As can be seen, commercial preparations, such as ISCADOR, do not meet the initial screening test and therefor are not pharmaceutical grade in accordance with the present invention. The ISCADOR extracts also do not meet the more stringent specific protein fingerprint requirements of the present method. However, the extracts n-T4GEN and T4GEN, which do meet the specific protein concentration fingerprint of the present invention, both have activity levels well above the minimum of 100 A.U. The screening procedure is preferred because it allows non-pharmaceutical grade extracts to be identified relatively quickly without having to conduct the more time consuming protein fingerprinting. Once an extract passes this initial screening step, it then still must meet the further protein fingerprint requirements in order to qualify as pharmaceutical grade in accordance with the present invention.

It is also preferred that the fraction of the extract which contains protein that does not bind to sugar be analyzed to provide a further fingerprint that may be used in identifying whether the extract is pharmaceutical grade. As shown in the FIGURE, a fraction containing unbound protein remains after separation of the sugar-binding proteins from the extract. This unbound protein fraction contains an "alkaloid" fraction and a viscotoxin fraction. These two fractions can be isolated from each other by column chromatography using a Sephadex G-75 column or equivalent. The amount of alkaloids in the alkaloid fraction should be about 10 to 50 µg per ml of 1 percent extract. The amount of viscotoxin in the protein fraction should be about 10 to 40 µg per ml of 1 percent extract. As previously described, a 1 percent extract is one where 1 gram of total initial non-dehydrated plant material is extracted with 100 ml of aqueous extractant. The amount of viscotoxins and alkaloidal proteins will increase proportionally as the amount of plant material extracted per 100 ml increases.

In use, the extracts may be used as is or diluted with suitable pharmaceutical carriers and administered according to known procedures for treating AIDS or a particular cancer. For treating AIDS, the extract is preferably injected subcutaneously in doses ranging from 0.01 to 1 ml of a 1 percent extract. Extracts which are more concentrated, such as 2 and 5 percent extracts, may be used. Extracts with even higher concentrations may also be used depending upon the dosage required. The injections are preferably given twice a week, but may be given more often. For cancerous tumors, the extract is injected directly into the tumor or may be injected subcutaneously.

An extract identified herein as n-T4GEN was tested to demonstrate its anti-HIV activity N-T4GEN was analyzed and found to meet the sugar-binding protein fingerprint set forth in TABLE 11. The amount of protein in the alkaloidal and viscotoxin fractions were also found to be within the required fingerprint ranges. The n-T4GEN extract was prepared from Korean mistletoe. n-T4GEN was added to culture wells in an amount sufficient to provide concentration of 1 µl of a 1 percent extract per ml of test solution (equivalent to 10 µg of extract per ml of test solution). This concentration of n-T4GEN inhibited HIV-induced cytopathic effects in H9 lymphoid human leukemia cells with concomitant reduction in viral reverse transcriptase levels in the infected cells.

Human immunodeficiency virus (HIV) infects T4 lymphocytes. In the H9 human lymphoma cell line, the virus produces giant multinucleated syncytial cells. After 3–6 days of viral infection, the number of syncytia correlates with the degree of virus growth as quantified in the presence and absence of the drug being tested. These cytopathetic effects and assay of viral reverse transcriptase were used to demonstrate anti-HIV effects of n-T4GEN.

The anti-HIV assay using 1 µl/ml of a 1 percent n-T4GEN extract per ml of test solution was conducted as follows:

HIV inoculum was standardized for reverse transcriptase (RT) activity using purified avian myeloblastosis viral RT (BRL Labs, Gaithersberg, Md.) and used to infect polybrene treated H9 cells at 0.02 RT units of HIV per $2 \times 10^6$ cells. The virus was adsorbed for 2 hours at 37° C. and then the cells were washed twice and resuspended in RPMI 1640 containing 10% fetal bovine serum at $2 \times 10^5$ cells/ml and dispersed in 1 ml aliquots into 24-well plates (Falcon Division, Beckton Dickinson Co., Cockneyville, Md.). Syncytial giant cell formation appeared at 5–6 days post infection, and this cytopathic effect (CPE) was quantitatively measured by dispersing 0.1 ml aliquots into 0.1 ml absolute methanol and enumerating the giant cells microscopically. The inhibition of CPE by antiviral treatment with 1 µl (10 µg) of a 1 percent n-T4GEN extract per 1 ml of test solution was compared to untreated, infected H9 cells.

Reverse transcriptase activity was measured using 1 ml culture aliquots which were clarified at 600 xg for 30 minutes, precipitated in 10% polyethylene glycol—0.13M NaCl at 4° C. for 18 hours, and centrifuged at 600 xg for 60 minutes. The pellet was dissolved in glycerol-Tris buffer (50% glycerol, 25 mM Tris HCl pH 7.5, 5 mM dithiothreitol, 15 mM KCl, 0.025% Triton-X, and 0.25 mM EDTA). The RT assay was adapted from the methods of J. Levy et al., Science 225, 840 (1984); D. D. Ho et al., ibid 226, 451 (1984) using a final reaction mixture containing 40 mM Tris-HCl pH 7.8, 2.2 mM dithiothreitol, 10 mM $MgCl_2$, 50 mM KCl, 0.03% Triton-X, 25 µCi $^3$H-thymidine triphosphate (New England Nuclear, Boston, Mass.), and 50 µg/ml poly rA oligo $^{dT}$12–18 (BRL, Gaithersburg, Md.). Background counts were determined using poly dA oligo $^{dT}$12–18 as template and subtracted from the poly rA dT primer cpm to determine the thymidine incorporation specifically due to RT-activity.

The results of the tests are set forth as follows:

| Effect of Mistletoe Extract on the Infectivity of HIV to H9 Lymphoma Cells in Culture | | |
|---|---|---|
| n-T4GEN* (µg/ml) | Cytopathic Effects (Syncytia cells) Day 5 | Reverse Transcriptase (cpm) Day 10 |
| 0.01 | ++ | 97,896 (100) |
| 0.10 | ++ | 77,971 (79) |
| 1.00 | ++ | 65,932 (67.3) |
| 10.00 | ± | 32,128 (32.8) |
| 100.00 | (toxic) | 4,200 |

H9 lymphoma cells growing in RPMI-1640 media containing 10% fetal calf serum were infected with HIV (100,000 RT counts) on day 1 and various concentrations of n-T4GEN extract. On day 5 cells were observed for cytopathic effects (syncytia), and on day 10 assayed for RT activity. (++) Denotes extensive giant cells, (±) fewer syncytial cell.
*Amounts expressed as µg of 1 percent extract per ml of cell culture.

The results show that n-T4GEN at non-toxic concentrations inhibited HIV-induced cytopathic effects on H9 lymphoma cells. At these concentrations (10 µg/ml) there was also a significant (67.2%) inhibition of the viral reverse transcriptase. An extract identified herein as T4GEN was tested along with n-T4GEN to demonstrate their anti-cancer activity. T4GEN was analyzed and found to meet the sugar-binding protein fingerprint set forth in TABLE 10. The amount of protein in the alkaloidal and viscotoxin fractions were also found to be within the required fingerprint ranges. The T4GEN extract was prepared from European mistletoe.

Anticancer activities of T4GEN and n-T4GEN were studied in animals bearing subcutaneous transplants of C3H Mammary adenocarcinoma 16/C. This tumor is maintained as a lung passed tumor in C3H female mice. In this example, tumors ($1 \times 10^6$ cells) were transplanted (S.C.) in 18–20 g B6C3F1 hybrid female mice. On the following day, the tumor bearing animals were randomized and separated into different treatment groups (10 mice per group). There were 15 animals in the control group who received only physiological saline during the treatment periods. The treatments (i.p.) were started 48 hours after the transplants and given for a duration of 14 days (daily single injections). Animals were weighed on days 5, 9 and 14 to assess toxic effects. Tumors were measured on days 21, 28, post transplants and the results are represented as tumor weights using formula $l \times w^2 / 2$ (l=length of tumor, w=width of tumor expressed in mm).

The results set forth below show that the T4GEN extract at a dose schedule equivalent to 1 ml of a 1 percent extract/kg (20 mg/kg), qd (1–14) caused a 98% inhibition in the growth of this tumor. In the same experiment the n-T4GEN (5 mg/kg, qd 1–14) caused 33% inhibition growth of mammary adenocarcinoma 16/C, however, 30% of the treated animals remained tumor free until the termination of the experiment (day 93). This animal model is an accepted model for human breast carcinomas. The results were as follows:

Effect of T4GEN and n-T4GEN on the Growth of Subcutaneous Transplants of C3H Mammary Adenocarcinoma 16/C in B6C3F1, Female Mice

| Treatments i.p. | Δ Wts (g) (day 14) | Tumor Wts (day 21) | Tumor Weight Inhibition % | Tumor Free Animals (day 93) |
|---|---|---|---|---|
| 1. Saline, Controls | +0.21 | 0.27 | — | 1/15 |
| 2. T4GEN* | | | | |
| 1 ml/kg, qd (1–14) | +0.82 | 0.15 | 44 | 0/10 |
| 2 ml/kg, qd (1–14) | −2.12 | 0.01 | 98 | 0/10 |
| 3. n-T4GEN* | | | | |
| .25 ml/kg, qd (1–14) | +1.33 | 0.15 | 44 | 1/10 |
| .50 ml/kg, qd (1–14) | +0.73 | 0.18 | 33 | 3/10 |
| 4. 5-Fluorouracil | | | | |
| 98 mg/kg, qd (1,7,14,21) | +1.77 | 0.00 | 100 | 0/6 |

*Amounts expressed as ml of 1 percent extract.

Examples of practice of the invention are as follows:

EXAMPLE 1

Preparation Of Pharmaceutical Grade Mistletoe Extract From Korean Mistletoe (n-T4GEN)

Plant powder (2.4 Kg) obtained from Korean mistletoe was extracted with 300 ml batches of water in a clean blender. The extract was filtered through cheese cloth lined filter beds to eliminate fibrous and water-insoluble residues, final volume 6.03 liters. Final concentration of the extract was 39.8% (plant weight/volume).

The extract was left at 4° C. for two weeks in absence of air (flushed with nitrogen). At this time additional insoluble residues were deposited. The cold extract was filtered through 0.8 μ filters and final sterile filtration was performed with 0.2 micron filters and in sterile environment. The semipurified product was collected in 500 ml sterile vacuum containers and identified as T4GEN. The product samples were found to be pyrogen free. Samples from the flask were removed with a sterile syringe in a laminar flow hood and diluted on the basis that each ml of the sample contains 400 mg of the extract (~40% solution).

The extract samples were analyzed according to the affinity chromatography system schematically shown in the FIGURE. The columns used to separate the proteins were Sepharose® 4B.

The columns were prepared as follows:

Activation of Sepharose 4B: Sepharose 4B (400 ml) was repeatedly washed with double distilled water and filtered on a buchner funnel. The sepharose residue was repeatedly washed with $Na_2 CO_3$ (0.5M, pH 11) and then suspended in a stirred 2 liter cylinder in 400 ml $Na_2 CO_3$ (0.5M, pH 11). The cylinder was covered with aluminum foil and to the stirred suspension of Sepharose 4B, divinylsulfone (48 ml, absence of light) was added dropwise over a period of 80 minutes. The reactants were stirred for another 30 minutes at room temperature. Then the resin was filtered on a sintered glass funnel (no touching with hands or paper) with approximately 500 ml of $Na_2 CO_3$ (0.5M, pH 10, make with $NaHCO_3$). At this time the resin was suspended in 400 ml $Na_2 CO_3$ (0.5M, pH 10) and used for preparing sugar-specific affinity resins as follows:

Galactose-specific Sepharose 4B: To the activated resin 380 ml (in 5M $Na_2 CO_3$), galactose (38 g) was added with stirring in absence of light. The suspension was stirred overnight and then the suspension was filtered on a sintered glass funnel. To inactivate the reacted activated sepharose, the residue was washed with 0.5M $NaHCO_3$ (pH 8.5) and then suspended in 350 ml $NaHCO_3$ (0.5M, pH 8.5) and 14 ml 2-mercaptoethanol. The stirred suspension was maintained at room temperature for 4 hours and then filtered on a sintered glass funnel. The resin was washed with 0.2M PBS (phosphate buffered saline) and finally suspended in 380 ml 0.2M PBS and stored at 4° C. along with a few crystals of $NaN_3$.

Lactose-specific Sepharose 4B: The method of preparation was the same as described for galactose. Here 300 ml of activated Sepharose was reacted with 30 g of lactose and the affinity resin was deactivated with 300 ml $NaHCO_3$ (0.5M, pH 8.5), 12 ml 2-mercaptoethanol and finally suspended in 300 ml of PBS and $NaN_3$ as described in the previous preparation.

N-Acetyl-D-galactosamine-specific Sepharose B: Activated Sepharose 4B (30 ml) was treated with 3 g of N-acetyl-D-galactosamine as described. The reaction was terminated with 30 ml $NaHCO_3$ (0.5M, pH 8.5) and 5 ml 2-mercaptoethanol. The resin was maintained in 30 ml PBS and a few crystals $NaN_3$ at 4° C.

Fucose-specific-Sepharose 4B: Activated Sepharose (50 ml) was reacted with 5 g fucose. The affinity resin was treated with 50 ml $NaHCO_3$ and 5 ml 2-mercaptoethanol to deactivate the unreacted Sepharose. The resin was maintained in 50 ml PBS and $NaN_3$ as described.

Melibiose-Specific Sepharose 4B: Activated Sepharose 4B (50 ml) was created with 5 g melibiose. The reaction was terminated with 50 ml $NaHCO_3$ and 5 ml mercaptoethanol. The resin was maintained in 50 ml PBS and a few crystals of $NaN_3$ at 4° C.

The same methods can be used to provide columns of different sugar specificity. The used columns were regenerated by elutions with 5M urea and followed by elution with 0.5M NaHCO$_3$ (pH 8.5). Prior to use, columns are equilibrated with 0.02M Tris/HCl buffer (Buffer C).

The Buffers used for Extraction and Affinity Chromatography were prepared as follows:

All buffers made in double distilled water (DD).

A) Tris/HCl (0.02M, pH 7.8) containing NaCl (0.2M) dithiothreitol (1 mM) and just use add phenyl methanesulfonyl fluoride (0.01 mM). (Buffer A).

B) Tris/HCl (0.02M, pH 7.8) containing 0.4M KCl, 2% Triton x-100, 1 mM dithiothreitol and 0.01 mM phenyl methanesulfonyl fluoride (to be added before use). (Buffer B).

C) Tris/HCl (0.02M, pH 7.8) containing 1.25M NaCl, 25 mM CaCl$_2$, 0.05% Triton x-100 and 1 mM dithiothreitol. (Buffer C).

D) Buffer (C) containing 4 mM EDTA instead of 25 mM CaCl$_2$. (Buffer D).

A known volume of the mistletoe extract was adjusted to pH 7.8 with 2M tris-buffer. The solution was absorbed on a series of Sepharose® 4B affinity columns (1.6×7 ml). The columns were washed with excess of (200 ml) of 0.02M tris-buffer (pH 7.8) containing 25 mM CaCl$_2$ (Buffer C) to remove all unbound proteins (viscotoxins and alkaloids). Then each column was separately washed with tris-buffer (pH 7.8) containing 4 mM EDTA (Buffer D) to elute proteins which require Ca$^{++}$ for their binding to specific sugars i.e. Ca$^{++}$ dependent sugar-binding proteins (100 ml samples). Subsequently, the columns were washed with tris-buffer (Buffer C, 200 ml) and then eluted with the same buffer (100 ml) containing 0.5M corresponding sugars to remove non-Ca$^{++}$ dependent sugar binding proteins. The unbound proteins were fractionated on a Sephadex G-75 column (2.5×75 cm) to separate viscotoxins from alkaloids. All fractions were dialyzed to remove salts and other buffer ingredients. Each dialyzed fraction was concentrated by Amicon concentrator using DIAFLO ultrafiltration membrane YM10 (10,000 cutoff). Protein concentration was measured by Bio-rad assay with bovine-globulin as a standard (each separated protein may be characterized for its purity and molecular weight by SDS page gel chromatography).

The inhibitory concentration (ID$_{50}$) was determined for each sugar-binding protein as follows:

Leukemia L1210 was maintained in asynchronous logarithmic growth at 37° C. in RPMI 1640 medium supplemented with 10% (v/v) fetal bovine calf serum and 1% (v/v) Pen Strep. The cell population doubling time was 11–12 hours. The cells were passed every 48 hours at 1×10$^4$ cell/ml in order to keep the cells in logarithmic stage of growth.

For all growth inhibition studies all stock solutions and dilutions were made with sterile 0.7% NaCl solution. The cell cultures were seeded at 2–5×10$^4$ cells/ml in duplicates for each inhibitor concentration in a microtiter plate (0.18 ml/well). The covered microtiter plate was incubated for 48 hours in a humidified CO$_2$ incubator containing 5% CO$_2$ in air. At the end of the incubation period, aliquots of each well were added to a measured volume of isotonic saline and counted in an electronic counter. Because fractions at high concentrations caused rapid cellular fragmentation, the test microtiter plates were routinely checked under a microscope prior to cell number counting so that the results were not compromised. The cell viability was determined by trypan blue exclusion. The results were calculated by plotting percent cell growth inhibition (as compared to the cell density of the saline treated controls) versus log of protein (or specific fraction) concentration which caused 50% inhibition (ID$_{50}$) in cell growth as determined from the graph.

The results of the analysis are shown in Tables 1 and 2 for n-T4GEN salt and detergent extracts prepared in accordance with this example. As can be seen from Tables 1 and 2, the extracts from both the sap and the cell walls of the Korean mistletoe have protein levels and inhibitory activities which all fall with the limits required to be identified as pharmaceutical grade extracts in accordance with the present invention. Accordingly, these extracts may be used in clinical studies directed to cancer or AIDS treatment. They may also be used for routine patient treatment since their quality and efficacy has been established in accordance with the protein fingerprint identifiers required by the present invention.

TABLE 1

FRACTIONATION OF THE VARIOUS CONSTITUENTS OF V. ALBUM COLORATUM WITH ANTILEUKEMIA - L1210 ACTIVITY - n-T4GEN (40 PERCENT EXTRACT) (Affinity Method, Fractionation of Salt Extract)

| Fraction identity | Protein Content (mg/ml) | Total Volume (ml) | Total Protein (mg) | ID$^a_{50}$ (µg Protein/ml) | Total Activity$^b$ Units |
|---|---|---|---|---|---|
| Salt Extract | 7.63 | 350 | 2673 | 0.11 | 2.4 × 10$^7$ |
| Affinity columns eluted with EDTA buffer - Ca$^{++}$ dependent | | | | | |
| | 0.31 | 20 | 6.24 | 0.38 | 1.6 × 10$^4$ |
| 1. Lactose | 0.39 | 20 | 7.91 | 0.25 | 3.1 × 10$^4$ |
| 2. Galactose | 0.28 | 20 | 5.44 | 0.20 | 2.7 × 10$^4$ |
| 3. Melibiose | 0.70 | 12.5 | 875 | 0.29 | 3.00 × 10$^4$ |
| 4. N-Acetyl-D-galactosamine | 0.28 | 18 | 5.04 | 0.36 | 1.4 × 10$^4$ |
| 5. Fucose | | | | | |
| Affinity columns eluted with corresponding sugars - non-Ca$^{++}$ dependent | | | | | |
| 1. Lactose | 0.27 | 22 | 5.98 | 0.00027 | 2.2 × 10$^7$ |
| 2. Galactose | 1.40 | 9 | 12.60 | 0.0013 | 9.6 × 10$^6$ |

TABLE 1-continued

FRACTIONATION OF THE VARIOUS CONSTITUENTS OF V. ALBUM COLORATUM WITH ANTILEUKEMIA - L1210 ACTIVITY - n-T4GEN
(40 PERCENT EXTRACT)
(Affinity Method, Fractionation of Salt Extract)

| Fraction identity | Protein Content (mg/ml) | Total Volume (ml) | Total Protein (mg) | $ID^a_{50}$ (µg Protein/ml) | Total Activity[b] Units |
|---|---|---|---|---|---|
| 3. Melibiose | 0.32 | 10 | 3.20 | 0.0034 | $9.4 \times 10^5$ |
| 4. N-Acetyl-D-galactosamine | 0.66 | 18 | 11.90 | 0.017 | $7.0 \times 10^5$ |
| 5. Fucose | 1.17 | 15 | 2.59 | 0.019 | $1.3 \times 10^5$ |
| Sephadex - G75 (Unbound proteins) Fractions[c] | | | | | |
| I (12–50) | 1.84 | 46 | 84.6 | 0.5 | $1.69 \times 10^5$ |
| II (51–70) | 1.22 | 22.5 | 27.45 | 4.0 | $6.8 \times 10^3$ |
| III (71–100) | 1.12 | 40 | 44.80 | 2.8 | $1.6 \times 10^4$ |
| IV (101–140)[d] | 0 | 50 | 0 | 13.5 | $1.6 \times 10^4$ |

[a]Inhibitory concentration expressed as µg protein/ml which caused 50% inhibition of the growth of L1210 cells in culture.
[b]Activity unit is defined as dilution factor needed for a specific fraction which when added to L1210 cells caused a 50% cell growth inhibition.
[c]50 ml on column from a total eluate of 325 ml.
[d]31 mg alkaloids obtained from fraction IV.

TABLE 2

FRACTIONATION OF THE VARIOUS CONSTITUENTS OF V. ALBUM COLORATUM WITH ANTILEUKEMIA - L1210 ACTIVITY
(40 PERCENT EXTRACT)
(Affinity Method, Fractionation of Detergent Extract)

| Fraction identity | Protein Content (mg/ml) | Total Volume (ml) | Total Protein (mg) | $ID^a_{50}$ (µg Protein/ml) | Total Activity[b] Units |
|---|---|---|---|---|---|
| Detergent Extract | 1.68 | 450 | 756 | 0.27 | $2.8 \times 10^6$ |
| Affinity columns eluted with EDTA buffer | | | | | |
| 1. Lactose | 0.18 | 22 | 4.04 | 0.250 | $1.6 \times 10^4$ |
| 2. Galactose | 0.08 | 11.5 | 0.97 | 0.031 | $3.1 \times 10^4$ |
| 3. Melibiose | 0.16 | 20 | 3.12 | 0.054 | $5.7 \times 10^4$ |
| 4. N-Acetyl-D-galactosamine | 0.17 | 19 | 3.20 | 0.076 | $4.2 \times 10^4$ |
| 5. Fucose | 0.12 | 6.5 | 0.78 | 0.100 | $0.5 \times 10^4$ |
| Affinity columns eluted with corresponding sugars | | | | | |
| 1. Lactose | 0.35 | 95 | 3.23 | 0.0045 | $2.1 \times 10^6$ |
| 2. Galactose | 0.50 | 15 | 7.50 | 0.0055 | $1.3 \times 10^6$ |
| 3. Melibiose | 0.15 | 12 | 0.61 | 0.0084 | $0.07 \times 10^6$ |
| 4. N-Acetyl-D-galactosamine | 0.62 | 4 | 7.68 | 0.0035 | $2.1 \times 10^6$ |
| 5. Fucose | 0.50 | 10 | 5.10 | 0.0500 | $0.1 \times 10^6$ |
| Sephadex - G75 (Unbound proteins) Fractions[c] | | | | | |
| I (9–35) | 1.58 | 33 | 52.1 | 1.25 | $0.05 \times 10^6$ |
| II (36–55) | 1.36 | 20 | 27.2 | 1.70 | $0.008 \times 10^6$ |
| III (56–120)[d] | 0 | 50 | 0 | 14.00 | $0.002 \times 10^6$ |

[a]Inhibitory concentration expressed as µg protein/ml which caused 50% inhibition of the growth of L1210 cells in culture.
[b]Activity unit is defined as dilution factor needed for a specific fraction which when added to L1210 cells caused a 50% cell growth inhibition.
[c]50 ml on column from a total eluate of 420 ml.
[d]22 mg alkaloids obtained from fraction III.

The protein containing fractions (12–100) with biological activity in L1210 system obtained from Sephadex G75 column (see Table 1) contained a mixture of viscotoxins (1.019 g). The fractions (101–140) were combined and extracted with 3×200 ml) chloroform. The chloroform layer was dried over anhydrous $Na_2SO_4$, filters and the filtrate was evaporated under vacuum to obtain 201 mg of alkaloids (weights of viscotoxins and alkaloids set forth in Table 1 are adjusted to a total of 325 ml for the unbound fraction obtained from affinity columns). Thus 1 ml of the 1 percent extract contained 4.9 µg lectins; 72 µg unbound proteins which contains from 10 to 40 µg of viscotoxins; and 14.3 µg alkaloids.

EXAMPLE 2

Preparation Of Pharmaceutical Grade Mistletoe Extract From European Mistletoe An extract of European mistletoe (*Viscum album L.*) was prepared and analyzed according to Example 1 except that only the aqueous salt extract was analyzed for its sugar-binding protein fingerprint. The extract is identified as T4GEN. The results of the fingerprint determination are set forth in Table 3. The T4GEN extract meets the requirement of the method of the present invention and therefor qualifies as a pharmaceutical grade extract.

Table 4 sets forth the analysis of ISCADOR® which is a fermented mistletoe extract. This fraction meets some but not all of the requirements of the present invention. For example, the bioactivity of the melibiose and fucose fractions are too low.

Table 5 shows the results of bioactivity assays for the T4GEN and ISCADOR® extracts where the $ID_{50}$ is expressed as the dilution factor needed per ml to cause 50% inhibition of L1210 cells in culture. Table 5 is derived from Tables 3 and 4 and shows the general drop in ISCADOR® activity compared to the unfermented European extract (T4GEN).

TABLE 3

FRACTIONATION OF BIOLOGICALLY ACTIVE CARBOHYDRATE BINDING PROTEINS FROM T4GEN

| Fraction identity | Protein Content (mg/ml) | Total Volume (ml) | Total Protein (mg) | $ID_{50}$[a] (µg Protein/ml) | Total Activity Units[b] |
|---|---|---|---|---|---|
| T4GEN (10%, FrF) Affinity columns eluted with BDTA buffer ($Ca^{++}$ dependent sugar-binding proteins) | 0.9 | 100 | 90 | 0.32 | $4.6 \times 10^5$ |
| 1. Lactose | 0.236 | 7 | 1.652 | 0.0337 | $0.49 \times 10^5$ |
| 2. Galactose | 0.040 | 9 | 0.360 | 0.0035 | $1.00 \times 10^5$ |
| 3. Melibiose | 0.052 | 4 | 0.208 | 0.0042 | $0.44 \times 10^5$ |
| 4. N-Acetyl-D-galactosamine | 0.128 | 8 | 1.024 | 0.080 | $0.12 \times 10^5$ |
| 5. Fucose | 0.920 | 8 | 0.734 | 0.050 | $0.14 \times 10^5$ |
| Affinity columns eluted with buffer containing corresponding sugars (Non-$Ca^{++}$ dependent sugar-binding proteins) | | | | | |
| 1. Lactose | 0.158 | 11 | 1.738 | 0.0079 | $2.2 \times 10^5$ |
| 2. Galactose | 0.128 | 10 | 1.280 | 0.0156 | $0.8 \times 10^5$ |
| 3. Melibiose | 0.200 | 8 | 1.600 | 0.345 | $0.4 \times 10^5$ |
| 4. N-Acetyl-D-galactosamine | 0.140 | 10 | 1.140 | 0.0044 | $3.2 \times 10^5$ |
| 5. Fucose | 0.148 | 9 | 1.332 | 0.360 | $0.36 \times 10^5$ |

[a]Inhibitory concentration expressed as µg protein/ml which caused 50% inhibition of the growth of L1210 cells in culture.
[b]Activity unit is defined as dilution factor needed for a specific fraction which when added to L1210 cells caused a 50% cell growth inhibition.

TABLE 4

FRACTIONATION OF BIOLOGICALLY ACTIVE CARBOHYDRATE BINDING PROTEINS FROM ISCADOR 'M', (20%)

| Fraction identity | Protein Content (mg/ml) | Total Volume (ml) | Total Protein (mg) | $ID_{50}$[a] (µg Protein/ml) | Total Activity Units[b] |
|---|---|---|---|---|---|
| Iscador 'M', 20% | 4.6 | 12 | 55 | 0.25 | $2.2 \times 10^5$ |
| Fractions from G-75 column (21–65) | 0.315 | 65 | 20.50 | 0.078 | $2.6 \times 10^5$ |
| Affinity columns eluted with EDTA buffer | | | | | |
| 1. Lactose | 0.203 | 10 | 2.08 | 0.39 | $0.57 \times 10^4$ |
| 2. Galactose | 0.064 | 12 | 0.70 | 0.07 | $0.63 \times 10^4$ |
| 3. Melibiose | 0.182 | 12 | 2.20 | 0.90 | $1.20 \times 10^4$ |
| 4. N-Acetyl-D-galactosamine | 0.048 | 12 | 0.50 | 0.29 | $0.35 \times 10^4$ |
| 5. Fucose | 0.151 | 9 | 1.36 | 0.28 | $0.80 \times 10^4$ |

TABLE 4-continued

FRACTIONATION OF BIOLOGICALLY ACTIVE CARBOHYDRATE BINDING PROTEINS FROM ISCADOR 'M', (20%)

| Fraction identity | Protein Content (mg/ml) | Total Volume (ml) | Total Protein (mg) | $ID_{50}$[a] (µg Protein/ml) | Total Activity Units[b] |
|---|---|---|---|---|---|
| Affinity columns eluted with buffer containing corresponding sugars | | | | | |
| 1. Lactose | 0.053 | 8.5 | 0.45 | 0.30 | $0.15 \times 10^4$ |
| 2. Galactose | 0.080 | 9 | 0.70 | 0.26 | $0.27 \times 10^4$ |
| 3. Melibiose | 0.009 | 7 | 0.06 | 0.035 | $0.17 \times 10^4$ |
| 4. N-Acetyl-D-galactosamine | 0.066 | 12.5 | 0.82 | 0.027 | $3.00 \times 10^4$ |
| 5. Fucose | 0.198 | 10.5 | 2.07 | 0.55 | $0.38 \times 10^4$ |
| Unbound proteins (after sugar buffer elution) | 0.225 | 50 | 11.25 | 0.25 | $4.5 \times 10^4$ |

[a] Inhibitory concentration expressed as µg protein/ml which caused 50% inhibition of the growth of L1210 cells in culture.
[b] Activity unit is defined as dilution factor needed for a specific fraction which when added to L1210 cells caused a 50% cell growth inhibition.

TABLE 5

EFFECT OF FERMENTATION ON THE BIOLOGICAL ACTIVITY OF CARBOHYDRATE BINDING PROTEINS (LECTINS) OF VISCUM ALBUM L. (ISCADOR 'M')

| Protein | T4GEN (A.U.) | ISCADOR (A.U.) | % Change (±) |
|---|---|---|---|
| ($Ca^{++}$ dependent sugar-binding proteins) | | | |
| 1. Lactose | $0.49 \times 10^5$ | $0.02 \times 10^5$ | −95.0 |
| 2. Galactose | $1.00 \times 10^5$ | $0.12 \times 10^5$ | −88.0 |
| 3. Melibiose | $0.44 \times 10^5$ | $0.07 \times 10^5$ | −84.1 |
| 4. N-Acetyl-D-galactosamine | $0.12 \times 10^5$ | $0.01 \times 10^5$ | −97.1 |
| 5. Fucose | $0.14 \times 10^5$ | $0.02 \times 10^5$ | −85.7 |
| (Non-$Ca^{++}$ dependent sugar-binding proteins) | | | |
| 1. Lactose | $2.20 \times 10^5$ | $0.20 \times 10^5$ | −91.0 |
| 2. Galactose | $0.80 \times 10^5$ | $0.02 \times 10^5$ | −97.5 |
| 3. Melibiose | $0.40 \times 10^5$ | $0.06 \times 10^5$ | −85.0 |
| 4. N-Acetyl-D-galactosamine | $3.20 \times 10^5$ | $0.72 \times 10^5$ | −77.5 |
| 5. Fucose | $0.36 \times 10^5$ | $0.01 \times 10^5$ | −97.3 |

*ISCADOR 'M', 20% and T4GEN (10%) were used as examples of fermented and unfermented mistletoe clinical preparations. Activity is described as total activity units as described elsewhere.

TABLE 6

GENERAL COMPOSITION REQUIREMENTS FOR PHARMACEUTICAL GRADE MISTLETOE EXTRACT

| | Percentage By Weight of Total Protein in Extract |
|---|---|
| ($Ca^{++}$ dependent sugar-binding proteins) | |
| 1. Lactose | 0.1–2.3 |
| 2. Galactose | 0.1–0.9 |
| 3. Melibiose | 0.1–0.6 |
| 4. N-Acetyl-D-galactosamine | 0.1–1.6 |
| 5. Fucose | 0.1–1.3 |
| (Non-$Ca^{++}$ dependent sugar-binding proteins) | |
| 1. Lactose | 0.1–2.4 |
| 2. Galactose | 0.1–1.9 |
| 3. Melibiose | 0.1–2.2 |
| 4. N-Acetyl-D-galactosamine | 0.1–2.8 |
| 5. Fucose | 0.1–2.0 |

TABLE 7

COMPOSITION REQUIREMENTS FOR PHARMACEUTICAL GRADE EUROPEAN MISTLETOE EXTRACT

| | Percentage By Weight of Total Protein in Extract |
|---|---|
| ($Ca^{++}$ dependent sugar-binding proteins) | |
| 1. Lactose | 1.3–2.3 |
| 2. Galactose | 0.1–0.9 |
| 3. Melibiose | 0.1–0.6 |
| 4. N-Acetyl-D-galactosamine | 0.5–1.6 |
| 5. Fucose | 0.3–1.3 |
| (Non-$Ca^{++}$ dependent sugar-binding proteins) | |
| 1. Lactose | 1.4–2.4 |
| 2. Galactose | 0.9–1.9 |
| 3. Melibiose | 1.2–2.2 |
| 4. N-Acetyl-D-galactosamine | 0.8–2.8 |
| 5. Fucose | 1.0–2.0 |

TABLE 8

COMPOSITION REQUIREMENTS FOR PHARMACEUTICAL GRADE KOREAN MISTLETOE EXTRACT

| | Percentage By Weight of Total Protein in Extract |
|---|---|
| ($Ca^{++}$ dependent sugar-binding proteins) | |
| 1. Lactose | 0.1–0.5 |

TABLE 8-continued

COMPOSITION REQUIREMENTS FOR PHARMACEUTICAL GRADE KOREAN MISTLETOE EXTRACT

| | Percentage By Weight of Total Protein in Extract |
|---|---|
| 2. Galactose | 0.1–0.5 |
| 3. Melibiose | 0.1–0.5 |
| 4. N-Acetyl-D-galactosamine | 0.1–0.5 |
| 5. Fucose | 0.1–0.5 |
| (Non-Ca$^{++}$ dependent sugar-binding proteins) | |
| 1. Lactose | 0.1–0.5 |
| 2. Galactose | 0.1–0.8 |
| 3. Melibiose | 0.1–0.5 |
| 4. N-Acetyl-D-galactosamine | 0.1–0.7 |
| 5. Fucose | 0.1–0.5 |

TABLE 9

GENERAL COMPOSITION REQUIREMENTS FOR PHARMACEUTICAL GRADE MISTLETOE EXTRACT

| | Concentration (mg/ml) | Inhibitory Concentration ($ID_{50}$) |
|---|---|---|
| (Ca$^{++}$ dependent sugar-binding proteins) | | |
| 1. Lactose | 0.1–0.5 | 0.01–0.5 |
| 2. Galactose | 0.01–0.5 | 0.001–0.5 |
| 3. Melibiose | 0.01–0.5 | 0.001–0.5 |
| 4. N-Acetyl-D-galactosamine | 0.1–1.0 | 0.01–0.5 |
| 5. Fucose | 0.1–1.0 | 0.01–0.5 |
| (Non-Ca$^{++}$ dependent sugar-binding proteins) | | |
| 1. Lactose | 0.1–0.5 | 0.0001–0.1 |
| 2. Galactose | 0.1–2.0 | 0.001–0.1 |
| 3. Melibiose | 0.1–0.5 | 0.001–0.5 |
| 4. N-Acetyl-D-galactosamine | 0.1–1.0 | 0.001–0.1 |
| 5. Fucose | 0.1–1.5 | 0.01–0.5 |

TABLE 10

COMPOSITION REQUIREMENTS FOR PHARMACEUTICAL GRADE EUROPEAN MISTLETOE EXTRACT

| | Concentration (mg/ml) | Inhibitory Activity ($ID_{50}$) |
|---|---|---|
| (Ca$^{++}$ dependent sugar-binding proteins) | | |
| 1. Lactose | 0.1–0.3 | 0.01–0.1 |
| 2. Galactose | 0.01–0.1 | 0.0001–0.01 |
| 3. Melibiose | 0.01–0.1 | 0.001–0.01 |
| 4. N-Acetyl-D-galactosamine | 0.1–0.3 | 0.01–0.1 |
| 5. Fucose | 0.5–1.0 | 0.01–0.1 |
| (Non-Ca$^{++}$ dependent sugar-binding proteins) | | |
| 1. Lactose | 0.1–0.3 | 0.001–0.1 |
| 2. Galactose | 0.1–0.3 | 0.01–0.1 |
| 3. Melibiose | 0.1–0.3 | 0.1–0.5 |
| 4. N-Acetyl-D-galactosamine | 0.05–0.3 | 0.001–0.01 |
| 5. Fucose | 0.05–0.3 | 0.1–0.5 |

TABLE 11

COMPOSITION REQUIREMENTS FOR PHARMACEUTICAL GRADE KOREAN MISTLETOE EXTRACT

| | Concentration (mg/ml) | Inhibitory Activity ($ID_{50}$) |
|---|---|---|
| (Ca$^{++}$ dependent sugar-binding proteins) | | |
| 1. Lactose | 0.1–0.5 | 0.1–0.5 |
| 2. Galactose | 0.2–0.6 | 0.1–0.5 |
| 3. Melibiose | 0.1–0.5 | 0.1–0.5 |
| 4. N-Acetyl-D-galactosamine | 0.5–1.0 | 0.1–0.5 |
| 5. Fucose | 0.1–0.5 | 0.1–0.5 |
| (Non-Ca$^{++}$ dependent sugar-binding proteins) | | |
| 1. Lactose | 0.1–0.5 | 0.0001–0.009 |
| 2. Galactose | 1.0–2.0 | 0.001–0.01 |
| 3. Melibiose | 0.1–0.5 | 0.001–0.01 |
| 4. N-Acetyl-D-galactosamine | 0.5–1.0 | 0.001–0.1 |
| 5. Fucose | 1.0–2.0 | 0.001–0.1 |

TABLE 12

BIOLOGICAL ACTIVITY OF MISTLETOE EXTRACTS IN TERMS OF ACTIVITY UNITS (A.U.)

| | Sample Identity | Activity units/ml, (1% Extract) |
|---|---|---|
| 1. | ISCADOR M, Arg., 10% | 80 |
| 2. | n-T4GEN, 40% | 400 |
| 3. | T4GEN, 5% | 227 |
| 4. | ISCADOR M, 5% | 30 |
| 5. | ISCADOR M, 20% | 37 |
| 6. | T4GEN, 1% | 140 |
| 7. | T4GEN, 10% | 217 |
| 8. | ISCADOR M, 20% | 26 |
| 9. | n-T4GEN, 40% | 416 |
| 10. | n-T4GEN | 192 |
| 11. | n-T4GEN | 811 |

$$\text{Activity unit per ml} = \frac{\text{concentration of sample in } \mu g/ml}{ID_{50} (\mu g/ml)}.$$

EXAMPLE 3

Preparation of Double Distilled Water Extract

An extract from Korean mistletoe was prepared by taking a known weight of plant (100 g) and cleaning and crushing it in the presence of double distilled water to form a 40% by weight solution of mistletoe. It is preferred that the plant be cut and the cuttings put in a plastic bag and flash frozen in liquid nitrogen prior to being crushed and combined with the distilled water. The crushing and combination of the frozen material with the distilled water is preferably carried out in a blender for about 2 minutes. The resulting mixture is centrifuged at 10,000 rpm for 65 minutes to separate extract from insoluble residue. The residue is twice extracted with known volumes (100 ml) of water to remove all extract and subjected to centrifugation. The supernatants are combined. The resulting extract is stored in the absence of air at room temperature for two weeks. The extract is then sterilized by step filtration as is conventionally known.

The sterile extract is then subjected to a preliminary screening test as previously described to determine if its bioactivity with respect to the L1210 leukemia system is 100 A.U. or more. If the extract passes this test, then it is subjected to the more rigorous tests as described in Examples 1 and 2 to determine its sugar-binding protein fingerprint. If the protein levels fall within the limits required in accordance with the present invention, then the extract is identified as pharmaceutical grade. Table 13 sets forth the results of testing of an extract prepared as above. As can be seen, the extract has concentration levels and percentages which fall within the limits required for it to be identified as pharmaceutical grade in accordance with the present invention.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

TABLE 13

FRACTIONATION OF DIFFERENT BIOLOGICALLY ACTIVE CARBOHYDRATE BINDING PROTEINS FROM VISCUM ALBUM C. EXTRACT (40%, FrF)(n-T4GEN)

| Fraction identity | Total Volume (ml) | Total Protein (mg) | $ID_{50}{}^a$ | $ID_{50}{}^a$ ($\mu$g/ml) | Total Activity Units[b] |
|---|---|---|---|---|---|
| Extract (40%, FrF) | 90 | 234 | 32,500 | | $2.92 \times 10^6$ |
| Affinity columns eluted with EDTA buffer | | | | | |
| 1. Lactose | 5.5 | 4.29 | 175 | 1.10 | $0.10 \times 10^4$ |
| 2. Galactose | 11.5 | 2.10 | 415 | 0.49 | $0.50 \times 10^4$ |
| 3. Melibiose | 10 | 1.36 | 315 | 0.40 | $0.30 \times 10^4$ |
| 4. N-Acetyl-D-galactosamine | 7 | 0.95 | 400 | 0.33 | $0.28 \times 10^4$ |
| 5. Fucose | 5 | 1.82 | 365 | 1.00 | $0.18 \times 10^4$ |
| Affinity columns eluted with buffer containing corresponding sugars | | | | | |
| 1. Lactose | 8 | 2.24 | 208,000 | 0.001 | $1.66 \times 10^6$ |
| 2. Galactose | 11 | 2.68 | 68,000 | 0.0035 | $0.75 \times 10^6$ |
| 3. Melibiose | 6.5 | 0.96 | 5,600 | 0.025 | $0.036 \times 10^6$ |
| 4. N-Acetyl-D-galactosamine | 4.5 | 0.81 | 49,000 | 0.0035 | $0.22 \times 10^6$ |
| 5 Fucose | 5 | 0.33 | 10,500 | 0.0056 | $0.052 \times 10^6$ |
| Unbound proteins and alkaloids | 168 | 285 | 1,600 | 1.25 | $0.27 \times 10^6$ |

[a]Dilution factor needed per ml to cause 50% inhibition of L1210 cells in culture.
[b]Activity unit is defined as dilution factor needed for a specific fraction which when added to L1210 cell will cause 50% inhibition of the cell growth.

EXAMPLE 4

Preparation of Total Extract of Korean Mistletoe

An extract of Korean mistletoe was prepared by taking 100 g of mistletoe, freezing it and powdering it. The frozen powder was then thawed and extracted with 200 ml of cold acetone. The extraction mixture was centrifuged at 10,000 rpm for 60 minutes. The precipitate was washed with two 100 ml aliquots of cold acetone and centrifuged again at 10,000 rpm for 60 minutes. The resulting extract residue is extracted with two 200 ml aliquots of Buffer A (see Example 1) in a blender for 2 minutes each. The two extract aliquots are centrifuged at 10,000 rpm for 60 minutes and the supernatants combined. The extract residue is extracted a final time with an additional 200 ml of Buffer A. After centrifugation, this final extractant is combined with the other two aliquots to form a salt extract which after removal of salts, is then tested in accordance with the present invention to determine if its sugar-binding protein fingerprint meets the pharmaceutical grade requirements set forth above.

The extract residue remaining after the above extraction with Buffer A may be extracted with a detergent extract -Buffer B (see Example 1)- to form an extract which, after dialysis to remove detergents and salts, also can be tested to determine if it meets the pharmaceutical grade requirements of the present invention.

The scientific articles and other references referred to in this specification are hereby specifically all incorporated by reference.

What is claimed is:

1. A method for making a pharmaceutical grade mistletoe extract, said method comprising the steps of:

extracting mistletoe with an aqueous solution to form an aqueous extract;

measuring the total concentration of protein in said extract;

measuring the concentration of one or more $Ca^{++}$ dependent sugar-binding proteins in said extract, said sugar-binding protein being selected from the group of proteins in said extract which binds to lactose, galactose, melibiose, N-acetyl-D-galactosamine and fucose; and determining the relative concentration of said one or more $Ca^{++}$ dependent sugar-binding proteins with respect to said total concentration of protein and identifying said aqueous extract as being of pharmaceutical grade only if the relative concentration of said one or more $Ca^{++}$ dependent sugar-binding proteins is between about 0.1 and 2.8 percent of total protein.

2. A method for making a pharmaceutical grade mistletoe extract, said method comprising the steps of:

extracting mistletoe with an aqueous solution to form an aqueous extract;

measuring the total concentration of protein in said extract;

measuring the concentration of one or more non-$Ca^{++}$ dependent sugar-binding proteins in said extract, said sugar-binding protein being selected from the group of proteins in said extract which binds to lactose, galactose, melibiose, N-acetyl-D-galactosamine and fucose; and determining the relative concentration of said one or more non-$Ca^{++}$ dependent sugar-binding proteins with respect to said total concentration of protein and identifying said aqueous extract as being of pharmaceutical grade only if the relative concentration of said one or more non-$Ca^{++}$ dependent sugar-binding proteins is between about 0.1 and 2.8 percent of total protein.

3. A method for making a pharmaceutical grade mistletoe extract according to claim 1 which includes the additional steps of measuring the concentration of one or more non-$Ca^{++}$ dependent sugar-binding proteins in said extract, said non-$Ca^{++}$ dependent sugar-binding protein being selected from the group of proteins in said extract which binds to lactose, galactose, melibiose, N-acetyl-D-galactosamine and fucose; and determining the relative concentration of said one or more non-$Ca^{++}$ dependent sugar-binding proteins with respect to said total concentration of protein and identifying said aqueous extract as being of pharmaceutical grade only if the relative concentration of said one or more non-$Ca^{++}$ dependent sugar-binding proteins is between about 0.1 and 2.8 percent of total protein.

4. A method for making a pharmaceutical grade mistletoe extract according to claim 1 which includes the additional steps of:

measuring the inhibitory concentration of said one or more $Ca^{++}$ dependent sugar-binding proteins in said extract; and identifying said aqueous extract as being of pharmaceutical grade only if the inhibitory concentration of said one or more $Ca^{++}$ dependent sugar-binding proteins is between about 0.001 and 0.50 µg/ml based on an approximately 40% aqueous extract of mistletoe.

5. A method for making a pharmaceutical grade mistletoe extract according to claim 2 which includes the additional steps of:

measuring the inhibitory concentration of said one or more non-$Ca^{++}$ dependent sugar-binding proteins in said extract; and identifying said aqueous extract as being of pharmaceutical grade only if the inhibitory concentration of said one or more non-$Ca^{++}$ dependent sugar-binding proteins is between about 0.001 and 0.50 µg/ml based on an approximately 40% aqueous extract of mistletoe.

6. A method for making a pharmaceutical grade mistletoe extract according to claim 3 which includes the additional steps of:

measuring the inhibitory concentration of said one or more $Ca^{++}$ dependent sugar-binding proteins in said extract;

measuring the inhibitory concentration of said one or more non-$Ca^{++}$ dependent sugar-binding proteins; and identifying said aqueous extract as being of pharmaceutical grade only if the inhibitory concentration of said one or more $Ca^{++}$ dependent sugar-binding proteins is between about 0.001 and 0.50 µg/ml and the inhibitory concentration of said one or more non-$Ca^{++}$ dependent sugar-binding proteins is between about 0.001 and 0.50 µg/ml based on an approximately 40% aqueous extract of mistletoe.

7. A method for making a pharmaceutical grade mistletoe extract according to claim 1 wherein said method comprises the steps of:

measuring the concentration of $Ca^{++}$ dependent protein in said extract which binds to galactose; and determining the relative concentration of said $Ca^{++}$ dependent protein which binds to galactose and identifying said aqueous extract as being of pharmaceutical grade only if the relative concentration of said $Ca^{++}$ dependent galactose binding proteins are between about 0.1 and 0.9 percent of total protein.

8. A method for making a pharmaceutical grade mistletoe extract according to claim 1 wherein said method comprises the steps of:

measuring the concentration of $Ca^{++}$ dependent sugar-binding protein in said extract which binds to melibiose; and determining the relative concentration of said $Ca^{++}$ dependent protein which binds to melibiose and identifying said aqueous extract as being of pharmaceutical grade only if the relative concentration of said $Ca^{++}$ dependent melibiose binding proteins are between about 0.1 and 0.6 percent of total protein.

9. A method for making a pharmaceutical grade mistletoe extract according to claim 1 wherein said method comprises the steps of:

measuring the concentration of $Ca^{++}$ dependent sugar-binding protein in said extract which binds to fucose; and determining the relative concentration of said $Ca^{++}$ dependent protein which binds to fucose and identifying said aqueous extract as being of pharmaceutical grade only if the relative concentration of said $Ca^{++}$ dependent fucose binding proteins are between about 0.1 and 1.3 percent of total protein.

10. A method for making a pharmaceutical grade mistletoe extract according to claim 1 wherein said method comprises the steps of:

measuring the concentration of $Ca^{++}$ dependent sugar-binding protein in said extract which binds to lactose; and determining the relative concentration of said $Ca^{++}$ dependent protein which binds to lactose and identifying said aqueous extract as being of pharmaceutical grade only if the relative concentration of said $Ca^{++}$ dependent lactose binding proteins are between about 0.1 and 2.3 percent of total protein.

11. A method for making a pharmaceutical grade mistletoe extract according to claim 1 wherein said method comprises the steps of:

measuring the concentration of $Ca^{++}$ dependent sugar-binding protein in said extract which binds to N-acetyl-D-galactosamine; and determining the relative concentration of said $Ca^{++}$ dependent protein which binds to N-acetyl-D-galactosamine and identifying said aqueous extract as being of pharmaceutical grade only if the relative concentration of said $Ca^{++}$ dependent N-acetyl-D-galactosamine binding proteins are between about 0.1 and 1.6 percent of total protein.

12. A method for making a pharmaceutical grade mistletoe extract according to claim 2 wherein said method comprises the steps of:

measuring the concentration of non-$Ca^{++}$ dependent sugar-binding protein in said extract which binds to galactose; and determining the relative concentration of said non-$Ca^{++}$ dependent protein which binds to galactose and identifying said aqueous extract as being of pharmaceutical grade only if the relative concentration of said non-$Ca^{++}$ dependent galactose binding proteins are between about 0.1 and 1.9 percent of total protein.

13. A method for making a pharmaceutical grade mistletoe extract according to claim 2 wherein said method comprises the steps of:

measuring the concentration of non-$Ca^{++}$ dependent sugar-binding protein in said extract which binds to melibiose; and     determining the relative concentration of said non-$Ca^{++}$ dependent protein which binds to melibiose and identifying said aqueous extract as being of pharmaceutical grade only if the relative concentration of said non-$Ca^{++}$ dependent melibiose binding proteins are between about 0.1 and 2.2 percent of total protein.

14. A method for making a pharmaceutical grade mistletoe extract according to claim 2 wherein said method comprises the steps of:

measuring the concentration of non-$Ca^{++}$ dependent sugar-binding protein in said extract which binds to fucose; and     determining the relative concentration of said non-$Ca^{++}$ dependent protein which binds to fucose and identifying said aqueous extract as being of pharmaceutical grade only if the relative concentration of said non-$Ca^{++}$ dependent fucose binding proteins are between about 0.1 and 2.0 percent of total protein.

15. A method for making a pharmaceutical grade mistletoe extract according to claim 2 wherein said method comprises the steps of:

measuring the concentration of non-$Ca^{++}$ dependent sugar-binding protein in said extract which binds to lactose; and     determining the relative concentration of said non-dependent protein which binds to lactose and identifying said aqueous extract as being of pharmaceutical grade only if the relative concentration of said non-$Ca^{++}$ dependent lactose binding proteins are between about 0.1 and 2.4 percent of total protein.

16. A method for making a pharmaceutical grade mistletoe extract according to claim 2 wherein said method comprises the steps of:

measuring the concentration of non-$Ca^{++}$ dependent sugar-binding protein in said extract which binds to N-acetyl-D-galactosamine; and     determining the relative concentration of said non-$Ca^{++}$ dependent protein which binds to N-acetyl-D-galactosamine and identifying said aqueous extract as being of pharmaceutical grade only if the relative concentration of said non-$Ca^{++}$ dependent N-acetyl-D-galactosamine binding proteins are between about 0.1 and 2.8 percent of total protein.

\* \* \* \* \*